United States Patent [19]  [11] Patent Number: 4,905,715
Johnson  [45] Date of Patent: Mar. 6, 1990

[54] PADDED LEG GUARD

[76] Inventor: Kathy J. Johnson, 3260 Burlington Ave., Oroville, Calif. 95966

[21] Appl. No.: 248,500

[22] Filed: Sep. 23, 1988

[51] Int. Cl.$^4$ .......................... A61F 13/00; A61F 3/00
[52] U.S. Cl. .................................... 128/882; 128/80 R
[58] Field of Search ................... 128/882, 80 R, 80 A, 128/80 C, 84 C, 89 R, 165, 77, 78

[56] References Cited

U.S. PATENT DOCUMENTS

| | | | |
|---|---|---|---|
| 901,592 | 10/1908 | Clegg | 128/165 |
| 1,471,948 | 10/1923 | Cox | 128/89 R |
| 1,786,862 | 12/1930 | Mouthe | 128/165 |
| 2,077,202 | 4/1937 | Barrie | 273/54 B |
| 2,746,051 | 5/1956 | Stahly | 128/80 R |
| 3,350,719 | 11/1967 | McClure, Jr. | 128/80 R |
| 3,387,305 | 6/1967 | Shafer | 128/80 R |
| 4,014,327 | 3/1977 | Spiro | 128/165 |
| 4,534,342 | 8/1985 | Paxa | 128/89 R |
| 4,790,299 | 12/1988 | Marquette | 128/80 C |

FOREIGN PATENT DOCUMENTS 1153613  5/1969  United Kingdom ............. 128/80 R

Primary Examiner—Robert A. Hafer
Assistant Examiner—Michael Brown

[57] ABSTRACT

A protective padding for prevention of human inner leg skin irritation is provided in a padded leg guard. The guard is formed in an I-shaped fabric panel having two outer layers of soft, non-abrasive material with one inner layer of cotton batting and one of flexible foam. Two rectangular horizontal panels connected by one vertical rectangular panel form the I-shape. The top horizontal panel is sized for attachment around the lower human thigh with the bottom horizontal panel sized slightly smaller for attachment around a human ankle. The vertical panel is sized in length for proper positioning of the top and bottom horizontal panels, and the width is structured for coverage of the inner calf. Adjustable attachments are provided by hook-and-loop fasteners which are positioned on the distal edges of the horizontal panels.

3 Claims, 1 Drawing Sheet

PADDED LEG GUARD

BACKGROUND OF THE INVENTION

1. Field of the Invention

This invention relates to padding devices designed to protect the human body. The invention is particularly directed towards knee and ankle padding used to prevent inner leg skin irritation prevalent to bed ridden and physically impaired patients.

2. Description of the Prior Art

Many people suffer from inner leg skin irritation due to a variety of causes, the most common being pressure sores suffered by bed-ridden elderly people and paralytic patients, especially when they are positioned on their side while sleeping. Limited mobility, poor circulation and overall poor skin condition contribute to skin breakdown simply from the weight and movement of one leg upon the other, particularly if that person is very thin and emaciated. Quite a few patients confined to convalescent hospitals and nursing homes experience inner leg skin irritation, especially those with limited mobility suffering from muscle contractures. The current accepted preventative procedure is to position bed pillows between the legs as protective padding, however displacement is always a constant problem due to movement of the patient. Others not residing in nursing homes who have a problem with frictional irritation of the inner knees can benefit from my invention, a padded device which is simple and easy to apply and which can be worn while walking, sitting or sleeping.

A wide variety of devices for applying padding to the human body are seen in the market place. Some are designed to prevent skin irritation and injury to the wearer, but the majority are provided in the form of protective sports shields primarily to protect the shin and not the inner knee and ankle area. A search was conducted at the U. S. Patent Office to see protective leg guards in general, and the past art patents produced were provided from the following classes and subclasses:

2/22, 59 and 36/2.

The following patents represented devices most pertinent to my invention:

1. Hart was issued U.S. Pat. No. 1,158,208, on Oct. 26, 1915, for an "Athletic Guard".
2. U.S. Pat. No. 2,338,424, was granted to Giardini on Jan. 4, 1944, for a "Limb Guard".
3. On Sept. 13, 1955, McMahan was issued Pat. No. 2,717,387, for a "Shin and Foot Guard".
4. Kremp was issued Pat. No. 3,533,106, on Oct. 13, 1970, for "Article for Protecting the Human Body Against Impacts".
5. On Dec. 11, 1979, Griffin was issued Pat. No. 4,177,806, for a "Knee Pillow".
6. U.S. Pat. No. 4,497,070, was granted to Cho on Feb. 5, 1985, for "Unitary Leg and Foot Protective Device".
7. Winer was issued U.S. Pat. No. 4,665,562, on May 19, 1987, for "Leg Protecting Apparatus".

Several of the past art patents disclosed pads designed for protective sports wear devised to shield a specific body part from an impact injury of some sort. These devices are therefore structured of stiff and nonresilient materials directed towards impact protection which would themselves cause pressure sores and irritation if worn for an extended period of time. Specific devices include U.S. Pat. Nos. 3,533,106, 2,727,387, and 2,338,424.

Some of the past art devices, including U.S. Pat. Nos. 2,727,387, and 2,338,424, are structured to provide protection for an area of the leg other than the inner knee and ankle. They would be completely impractical if applied to the inner knee due to the structure and shape of their desgin and the firm non-resilient materials of which they are manufactured.

Several of the patents produced in the search provided devices which could be utilized as knee or ankle padding but are not designed to do both simultaneously. The Hart patent, U.S. Pat. No. 1,158,208, the Winer patent, U.S. Pat. No. 4,665,562, the Cho patent, U.S. Pat. No. 4,497,070, and the Griffin patent, U.S. Pat. No. 4,177,806, show devices not long enough to cover both knee and ankle simultaneously. The Griffin device is also curved so as to be applied to a bent knee only and could not be easily worn while sitting or walking. The Cho patent is only designed to protect the front and sides of the leg and top of the foot and not the inner knee. The foot covering and attachment straps would make the device too time consuming to apply and the thin string attachments would prove restrictive to circulation.

One final major disadvantage of all the past art devices is the use of straps as the connecting means. Since a majority of people targeted for this type of leg protection are easily susceptible to skin irritation, the thin, narrow unpadded ties and straps provided in the past art devices can themselves cause excessive pressure and abrasion. Many of the people I have designed my invention for are debilitated and have poor circulation to begin with, and application of the past art devices could conceivably restrict blood circulation or cause decubitus ulcers. None of the devices provided in the search supplied padded attachment straps or padded ties, nor was the harmful effects of using unpadded attachment straps on debilitated people considered.

I therefore feel that none of the afore mentioned devices could be substituted in whole or in combinations for my device and produce the full scope of benefits and advantages provided by my invention.

SUMMARY OF THE INVENTION

In practicing my invention, I have developed a non-restrictive padded leg guard comprised of two outer layers of soft fabric overlaying a layer of resilient cotton batting and a layer of thin flexible foam. This protective fabric padding is structured in the form of an I-shaped panel having the top upper horizontal section of the "I" longer in length and sized for attachment around the thigh. The lower horizontal section of the I-shaped panel is sized smaller for attachment around the ankle. The middle vertical panel is of sufficient length for positioning the top horizontal panel over the knee and the bottom horizontal panel over the ankle. Each outward end of both horizontal sections are affixed with Velcro-brand or similar type fasteners which are designed to be positioned on the outside of the leg when in use to prevent pressure areas.

Therefore, it is a primary object of my invention to provide a padded leg guard which prevents skin irritation to the inner leg area resulting from a variety of causes.

A further object of my invention is to provide a padded leg guard which is non-confining and does not restrict blood circulation or normal range of motion.

Another object of my invention is to provide a padded leg guard which will not become displaced due to normal movement of the legs, being applied with nonrestrictive adjustable attachment means.

A still further object of my invention is to provide a padded leg guard which is easy to apply without assistance and can also be worn under or over loose clothing while walking, sitting or reclining.

An even further object of my invention is to provide a padded leg guard which is soft, flexible and resilient, yet also strong and durable, being manufactured of machine washable and dryable fabric.

A still further object of my invention is to provide a padded leg guard which is cost effective to manufacture.

Other objects and advantages of my device will become apparent from reading the specification and comparing numbered parts described with like numbered parts illustrated in the accompanying drawings.

Figures 1, 2:
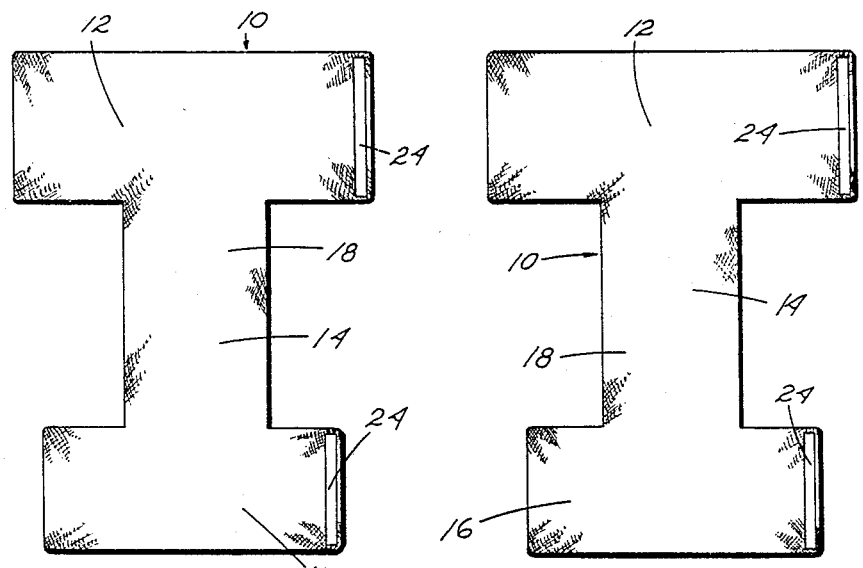
FIG. 1 is a view of the outside of the invention.
FIG. 2 is a view of the inside of the invention.

DRAWING REFERENCE NUMBERS 10 padded leg guard
12 horizontal top panel
14 vertical mid-panel
16 horizontal bottom panel
18 soft fabric
20 cotton batting
22 flexible foam
24 Velcro-brand fasteners
26 leg
28 knee
30 calf
32 ankle

DESCRIPTION OF THE PREFERRED EMBODIMENT

Figures 3, 4:
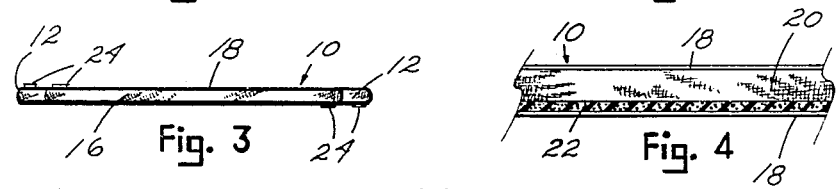
FIG. 3 is a bottom end view.
FIG. 4 is a cross-sectional view showing the component layers of the device, where the top surface represents the outside of the padded leg guard.
Figure 5:
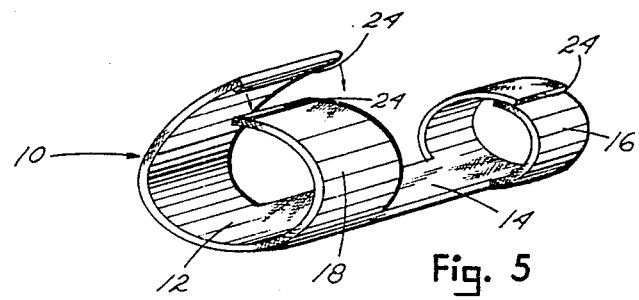
FIG. 5 is a perspective view illustrating the method of attachment.
Figure 6:
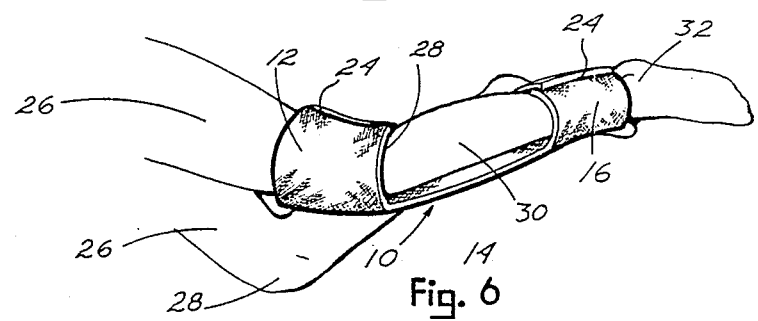
FIG. 6 is an in use view of the invention being worn on the right leg.

Referring now to the drawings and to FIG. 1 where the preferred embodiment of padded leg guard 10 is shown in a frontal view. Padded leg guard 10 is structured in the form of a thin I-shaped fabric panel, having a substantially rectangular horizontal top panel 12, a substantially rectangular vertical mid-panel 14, and a substantially rectangular horizontal bottom panel 16, shown in all views. Horizontal top panel 12 and horizontal bottom panel 16 have inside and outside surfaces, a top and bottom lengthwise edge, and two endward side edges. Vertical mid-panel 14 has an inside and outside surface, a top and bottom endward edge, and two lengthwise side edges. Horizontal top panel 12 is centrally edgewardly attached to the top endward edge of vertical mid-panel 14, which in turn is attached on the bottom endward edge to the central top lengthwise edge of horizontal bottom panel 16. Padded leg guard 10 is structured of four layers of material, as seen in FIG. 4. The two outer layers are soft fabric 18. The two inner layers comprise cotton batting 20 and flexible foam 22. The two outer layers of soft fabric 18 are connected by conventional sewing means. Horizontal top panel 12 is sized for circumferential attachment around knee 28, and horizontal bottom panel 16 is sized slightly smaller for circumferential attachment around ankle 32, as shown in FIG. 6. Vertical mid-panel 14 is positioned lengthwise with inside surface over the inner aspect of calf 30 and sized in length for proper positioning of horizontal top panel 12 above knee 28 and horizontal bottom panel 16 over ankle 32, also shown in FIG. 6. Placement of horizontal top panel 12 can also be made directly over knee 28 although placement slightly above knee 28 helps to prevent binding from the added bulk when knee 28 is bent. The shape of this device is significant in that although vertical mid-panel 14 could have been sized wider to surround entire calf 30, the unique I-shape is actually more efficient. There is greater air circulation with this design which prevents perspiration and chafing, and the reduced bulk of material is lighter and less apt to cause binding. Also less material and shorter sections of fasteners are required which help to reduce costs. The attachment means are provided by hook-and-loop fasteners with Velcro-brand fasteners 24, shown in FIG. 1, 2 and 5 being a satisfactory fastener. The Velcro-brand fasteners 24 are located to the front and back of the outer ends of horizontal top panel 12 and horizontal bottom panel 16. Although Velcro-brand fasteners 24 are shown in narrow vertical strips only, I have anticipated the fact that wider strips or horizontal placement of the fasteners could also be provided to allow for a wider degree of adjustability. The preferred embodiment of the invention is provided in various sizes to accommodate the diversity in sizes and shapes of users.

In use, padded leg guard 10 is positioned with the inside surface on the inner aspect of leg 26, as seen in FIG. 6. If the wearer is laying on his or her side, placement of padded leg guard 10 is made on the top or upper leg 26 with Velcro-brand fasteners 24 positioned to the outer aspect of leg 26 to prevent the development of pressure areas caused by the added bulk of Velcro-brand fasteners 24.

Although I have described my invention in detail in the specification it is to be understood that changes in structure and design may be practiced which do not exceed the intended scope of the appended claims.

What I claim as my invention is:
1. A padded leg guard for preventing skin irritation to the inner legs of humans comprising an I-shaped fabric panel including in attached combination:
a first longitudinally horizontally inclined substantially rectangular panel designated top panel;
a narrow longitudinally vertically inclined substantially rectangular panel designated mid-panel;
a second longitudinally horizontally inclined substantially rectangular panel designated bottom panel;
said attached combination being said top panel affixed centrally along a downwardly edge to an upwardly end of said narrow mid-panel with said mid-panel affixed by a downwardly end centrally to an upwardly edge of said bottom panel; said top panel sized and of a length for wraparound fitting to an upper human leg adjacent the knee; said bottom panel sized and of a length for wraparound fitting to a lower human leg adjacent the ankle; said narrow mid-panel of a length to span protectively the innerfacing side of a human leg maintaining said top panel and said bottom panel in wraparound attachment at fixed positions in the vicinity of said human knee and said human ankle; said I-shaped fabric panel structured with an external surface of soft fabric backed by a similar second layer of soft fabric and said soft fabric layers encasing a cotton batting layer covering a flexible foam pad core;

means for removably and adjustably retaining said top panel and said bottom panel in said wraparound attachment;

means for custom adjustment of said I-shaped fabric panel to accommodate various human leg sizes.

2. The padded leg guard of claim 1 wherein said means for removably and adjustably retaining said top panel and said bottom panel in said wraparound attachment includes adjustable, releasable connection of hook-and-loop type fasteners; said fasteners located edgewardly on distal end sections of said top panel and said bottom panel with a satisfactory hook-and-loop connector being Velcro-brand type fastener.

3. The padded leg guard of claim 1 wherein said means for custom adjustment of said I-shaped fabric panel to accommodate various human leg sizes is variation in the length of said narrow mid-panel in a variety of available models of said padded leg guard.

* * * * *